US006979307B2

(12) United States Patent
Beretta et al.

(10) Patent No.: US 6,979,307 B2
(45) Date of Patent: Dec. 27, 2005

(54) SYSTEMS AND METHODS FOR PREPARING AUTOLOGOUS FIBRIN GLUE

(75) Inventors: Roberto Beretta, Via Rho 8, 20125 Milano (IT); Nicholas A. Grippi, Wayne, NJ (US)

(73) Assignees: Cascade Medical Enterprises LLC, Wayne, NJ (US); Roberto Beretta, Milan (IT)

( * ) Notice: Subject to any disclaimer, the term of this patent is extended or adjusted under 35 U.S.C. 154(b) by 246 days.

(21) Appl. No.: 10/053,247

(22) Filed: Jan. 15, 2002

(65) Prior Publication Data

US 2002/0169408 A1 Nov. 14, 2002

Related U.S. Application Data

(63) Continuation-in-part of application No. 09/446,729, filed as application No. PCT/IT98/00173 on Jun. 24, 1998, now Pat. No. 6,368,298.

(30) Foreign Application Priority Data

Jun. 24, 1997 (IT) .......................... MI97A1490

(51) Int. Cl.$^7$ .......................... A61M 37/00; A61M 5/00; A61K 35/16; B01D 33/15; A61B 19/00

(52) U.S. Cl. .......................... 604/6.01; 604/7; 604/411; 604/414; 604/416; 424/529; 210/782; 210/515; 210/518; 600/576

(58) Field of Search ............................ 424/96.64, 530, 424/532, 533, 548; 435/6; 436/45, 63; 422/72–3, 44, 61, 68.1, 99–104; 604/4.01, 5.01, 6.01, 6.04, 6.16, 7, 81–85, 88–9, 522, 264–65, 317, 319, 321, 327, 403, 900, 407–416; 600/573–577; 606/213–215; 530/380–82

(56) References Cited

U.S. PATENT DOCUMENTS 1,593,814 A  7/1926  Vogel
3,604,410 A  9/1971  Whitacre (Continued)

FOREIGN PATENT DOCUMENTS

EP  0 580 094 A1  1/1994
EP  0 592 242 A1  4/1994

(Continued)

OTHER PUBLICATIONS

Bernstein, Lori R., et al., "Migration of Cultured Vascular Cells in Response to Plasma and Platelet–Derived Factors", Departments of Physiology and Surgery, Harvard Medical School, Children's Hospital Medical Center, J. Cell Sci. 56, 1982, pp. 71–82.

(Continued)

*Primary Examiner*—Patricia Bianco
(74) *Attorney, Agent, or Firm*—Michael Best & Friedrich LLP

(57) ABSTRACT

The invention provides a system for preparing an autologous solid-fibrin web suitable for regenerating tissue in a living organism. The system includes a sealed primary container containing a separation medium and a low-density high-viscosity liquid. The separation medium separates red blood cells from plasma when the container contains blood and is centrifuged, and the primary container has a first pressure. The system further includes a sealed secondary container containing a calcium-coagulation activator. The secondary container has a second pressure that is less than the first pressure. The system also comprises a transfer device including a cannula having a first end and a second end. The first and second ends puncture the sealed primary and secondary containers in order to provide fluid communication between the first and second containers. The low-density high-viscosity liquid of the primary container blocks flow through the cannula upon entering therein.

15 Claims, 8 Drawing Sheets

U.S. PATENT DOCUMENTS

| | | | |
|---|---|---|---|
| 3,654,925 A | * 4/1972 | Holderith | 604/413 |
| 3,939,822 A | 2/1976 | Markowitz | |
| 4,050,451 A | 9/1977 | Columbus | |
| 4,091,802 A | 5/1978 | Columbus | |
| D253,190 S | 10/1979 | Bixler et al. | |
| 4,322,298 A | 3/1982 | Persidsky | |
| 4,342,341 A | 8/1982 | Lee | |
| 4,356,958 A | 11/1982 | Kolobow et al. | |
| 4,369,117 A | 1/1983 | White | |
| 4,419,089 A | 12/1983 | Kolobow et al. | |
| 4,485,096 A | 11/1984 | Bell | |
| 4,564,359 A | 1/1986 | Ruhland | |
| 4,639,316 A | 1/1987 | Eldegheidy | |
| 4,861,477 A | 8/1989 | Kimura | |
| 4,865,733 A | 9/1989 | Tsuru et al. | |
| 5,030,215 A | 7/1991 | Morse et al. | |
| 5,037,549 A | 8/1991 | Ballies | |
| 5,065,768 A | 11/1991 | Coleman et al. | |
| 5,066,286 A | 11/1991 | Ryan | |
| 5,163,582 A | 11/1992 | Godolphin et al. | |
| 5,165,938 A | 11/1992 | Knighton | |
| 5,185,001 A | 2/1993 | Galanakis | 604/5 |
| 5,211,310 A | 5/1993 | Godolphin et al. | |
| 5,246,666 A | 9/1993 | Vogler et al. | |
| 5,257,633 A | 11/1993 | Vogler et al. | |
| 5,322,515 A | 6/1994 | Karas et al. | |
| 5,326,535 A | 7/1994 | Vogler et al. | |
| 5,354,483 A | 10/1994 | Furse | |
| 5,378,431 A | 1/1995 | Vogler et al. | |
| 5,389,265 A | 2/1995 | Luoma, II | |
| 5,413,246 A | 5/1995 | Godolphin et al. | |
| 5,419,835 A | 5/1995 | Adams et al. | |
| 5,455,009 A | 10/1995 | Vogler et al. | |
| 5,456,885 A | 10/1995 | Coleman et al. | |
| 5,533,518 A | 7/1996 | Vogler | |
| 5,555,920 A | 9/1996 | Godolphin et al. | |
| 5,560,830 A | 10/1996 | Coleman et al. | |
| 5,578,459 A | 11/1996 | Gordon et al. | |
| 5,585,007 A | 12/1996 | Antanavich et al. | |
| 5,588,946 A | 12/1996 | Graham et al. | |
| 5,599,718 A | 2/1997 | Gorog | |
| 5,634,474 A | 6/1997 | Grippi | |
| 5,634,893 A | 6/1997 | Rishton | |
| 5,643,192 A | 7/1997 | Hirsh et al. | |
| 5,674,458 A | 10/1997 | Holm | |
| 5,733,545 A | 3/1998 | Hood, III | |
| 5,736,033 A | * 4/1998 | Coleman et al. | 210/122 |
| 5,738,670 A | 4/1998 | Grippi | |
| 5,739,288 A | 4/1998 | Edwardson et al. | 530/382 |
| 5,763,410 A | 6/1998 | Edwardson et al. | 514/21 |
| 5,772,643 A | 6/1998 | Howell et al. | |
| 5,795,571 A | 8/1998 | Cederholm-Williams et al. | |
| 5,853,600 A | 12/1998 | McNeal et al. | |
| 5,935,051 A | 8/1999 | Bell | |
| 5,962,420 A | 10/1999 | Edwardson et al. | 514/21 |
| 6,010,627 A | 1/2000 | Hood, III | |
| 6,063,297 A | 5/2000 | Antanavich et al. | |
| 6,083,383 A | 7/2000 | Huang et al. | |
| 6,153,104 A | 11/2000 | Robertson | |
| 6,225,123 B1 | * 5/2001 | Cohen et al. | 436/17 |
| 6,234,948 B1 | 5/2001 | Yavilevich | |
| 6,238,578 B1 | 5/2001 | Fiehler | |
| 6,277,060 B1 | 8/2001 | Neumann | |
| 6,368,298 B1 | 4/2002 | Beretta | |
| 6,406,671 B1 | 6/2002 | DiCesare et al. | |
| 6,569,204 B1 | 5/2003 | Aldecoa | |

FOREIGN PATENT DOCUMENTS

| | | |
|---|---|---|
| EP | 0 580 094 B1 | 10/1996 |
| EP | 0 740 155 A1 | 10/1996 |
| EP | 0 512 612 B1 | 2/1998 |
| IT | 01 292 410 | 2/1999 |
| JP | 2504915 | 5/1994 |
| WO | WO 94/22503 | 10/1994 |
| WO | WO 95/12371 | 5/1995 |
| WO | WO 96/17871 | 6/1996 |
| WO | WO 96/27397 | 9/1996 |
| WO | WO 98/11925 | 3/1998 |
| WO | WO 98/58689 | 12/1998 |

OTHER PUBLICATIONS

Zetter, Bruce R., et al., "Stimulation of Human Vascular Endothelia Cell Growth by a Platelet Derived Growth Factor and Thrombin", Journal of Supramolecular Structure 11, 1979, pp. 361–370.

Knighton, David R., et al., "Platelet–Derived Angiogenesis: Initiator of Healing Sequence", Department of Surgery, School of Medicine, University of California, San Francisco, 1980, pp. 226–228.

Seppä, Heikki, et al., "Platelet–derived Growth Factor is Chemotactic for Fibroblasts", The Journal of Cell Biology, vol. 92, Feb. 1982 pp. 584–588.

Senior, Robert, M., "Chemotactic Activity of Platelet Alpha Granule Proteins for Fibroblasts", The Journal of Cell Biology, vol. 96, Feb. 1983, pp. 382–385.

Gospodarowicz, Denis, "Humoral Control of Cell Proliferation: The Role of Fibroblast Growth Factor in Regeneration, Angiogenesis, Wound Healing, and Neoplastic Growth", Department of Molecular Endocrinology, Salk Institute for Biological Studies, San Diego, California, 1976, pp. 1–19.

Franklin JD, Lynch JB, "Effects of topical application of epidermal growth factor on wound healing", *Plastic and Reconstructive Surgery*, Dec., 1979, pp. 766–770.

Buckley A, Davidson JM, "Sustained release of epidermal growth factor accelerates wound repair", *Proceeding National Academy Science USA*, vol. 82, pp. 7340–7344, Nov. 1985.

Sporn MB, Roberts AB, "Polypeptide transforming growth factors isolated from bovine sources and used for wound healing in vivo", *Science*, vol. 219, pp. 1329–1331, Mar. 18, 1983.

Canalis E, "Effect of Platelet–derived growth factor on DNA and protein synthesis in cultured rat calvaria", *Metabolism*, vol. 30, No. 10, pp. 970–975, Oct. 1981.

Niewiarowski S, Markiewicz, "Inhibition of the platelet–dependent fibrin retraction by the fibrin stabilizing factor (FSF, factor XIII)", *Journal of Laboratory and Clinical Medicine*, vol. 81, No.6, pp. 641–650, May 1973.

Li AKC, Koroly MJ, "Mechanical and humoral factors in wound healing", *British Journal of Surgery*, vol. 68, pp. 738–743, 1981.

Niewiarowski S, Millman M, "Potentiation of the thrombin induced platelet release reaction by fibrin", *Thrombosis Research*, vol. 9, No. 2, pp. 181–190, 1976.

Carroll RC, Gerrard JM, "Clot retraction facilitates clot Lysis", *Blood*, vol. 57, No. 1, pp. 44–48, Jan. 1981.

Joist JH, Niewiarowski S, "Retention of platelet fibrin stabilizing factor during the platelet release reaction and clot retraction", *Thrombos. Diathes. Haemorrh.*, vol. 29, pp. 679–683, 1973.

Niall M, Ryan GB, "The effect of epidermal growth factor on wound healing in mice", *Journal of Surgical Research*, vol. 33, No. 2, pp. 164–169, Aug. 1982.

Cazenave JP, Packham MA, "Inhibition of platelet adherence to a collagen–coated surface by agents that inhibit platlet shape change and clot retraction", *Journal of Laboratory and Clinical Medicine*, vol. 84, No. 4, pp. 483–493, Oct. 1974.

Niewiarowski S, Stewart GJ, "Effect of ADP and thrombin on fibrin retraction induced by human platelets and fibroblasts", *Thromb Diathes Haemorrh*, vol. 34, pp. 316–317, Oct. 1974.

Niewiarowski S, Goldstein S, "Fibrin clot retraction by human skin fibroblasts: effects of ADP and thrombin", *Proceedings of the Society for Experimental Biology and Medicine*, vol. 151, pp. 253–256, 1976.

Cohen I, Gabbay J, "Fibrin–blood platelet interaction in a contracting clot", *Thromb Diath Haemorrh*, vol. 34, No. 2, pp. 559, Nov. 15, 1975.

Dhall TZ, Shah GA, "Fibrin network structure: modification by platelets", *Thrombosis and Haemostasis*, vol. 49, No. 1, pp. 42–46, 1983.

Niewiarowski S, Gegoeczi E, "Platelet interaction with fibrinogen and fibrin: comparison of the interaction of platelets with that of fibroblasts, leukocytes and erythrocytes", *Annals of the New York Academy of Sciences*, vol. 201, pp. 72–83, 1972.

Knighton DR, Hunt TK, "Role of platelets and fibrin in the healing sequence: an in vivo study of angiogenesis and collagen synthesis", *Annals of Surgery*, vol. 196, No. 4, pp. 379–388, Oct. 1982.

Doni MG, Fantin G, "Thrombin–induced calcium and magnesium platlet release and clot retraction", *Haematologica*, vol. 60, No. 3, pp. 286–299, Sep. 1975.

Jelenska M, Kopec M, "Blood platelets cause retraction of collagen gel", *Thrombosis and Haemostasis*, vol. 44, No. 3, pp. 161–164, 1980.

Table Of Contents, *Thrombosis et Diathesis Haemorrhagica*.

Lundblad RL, "A rapid method for the purification of bovine thrombin and the inhibition of the purified enzyme with phenylmethylsulfonyl fluoride", *Biochemistry*, vol. 10, No. 13, pp. 2501–2506, Jun. 22, 1971.

Chao FC, Tullis JL, "Concentration effects of platelets, fibrinogen and thrombin on platelet aggregation and fibrin clotting", *Thromb Diathes Haemorrh*, vol. 32, No. 1, Sep. 30, 1974.

Solum, "Platelet aggregation during fibrin polymerization", *Scandinavian Journal of Clinical & laboratory Investigation*, vol. 18, No. 6, pp. 577–587, 1966.

Tashjian, "Platelet–derived growth factor stimulates bone resorption via a prostaglandin–mediated mechanism", *Endocrinology*, vol. 111, No. 1, pp. 118–124, 1982.

Mustard JF, Perry DW, "Factors responsible for ADP–induced release reaction of human platelets", *American Journal of Physiology*, vol. 228, No. 6, Jun. 1975.

Day HJ, Ang G, "Platelet release reaction during clotting of native human platelet–rich plasma", *Proceedings of the Society of Experimental and Biological Medicine*, vol. 139, No. 3, pp. 717–721, Mar. 1972.

Niewiarowski S, Stewart GJ, "ADP, thrombin and Bothrops atrox thrombin like enzyme in platelet–dependent fibrin retraction", *American Journal of Physiology*, vol. 229, No. 3, pp. 737–745, Sep. 1975.

Mustard JF, Perry DW, "Preparation of suspensions of washed platelets from humans", *British Journal of Haematology*, vol. 22, No. 2, pp. 193–204, Feb. 1972.

Packham MA, Guccione MA, "Platelet aggregation and release: effects of low concentrations of thrombin or collagen", *American Journal of Physiology*, vol. 225, No. 1, pp. 38–47, Jul. 1973.

Niewiarowski S, Thomas DP, "Platelet aggregation by ADP and thrombin", *Nature*, vol. 212, pp. 1544–1547, Dec. 31, 1966.

Thorton JW, Hess CA, "Epidermal growth factor In the healing of second degree burns: a controlled animal study", *Burns*, vol. 8, No. 3, pp. 156–160, 1983.

Holmsen H, Day HJ, "The blood platelet release reaction", *Scandinavian Journal of Haematology (Supplement K)*, pp. 3–21, 1969.

Rosenthal AR, Harbury C, "Use of a platelet–fibrinogen–thrombin mixture as a corneal adhesive: experiments in sutureless lamellar keratoplasty in the rabbit", *Investigative Ophthalmology*, vol. 14, No. 11, pp. 872–875, Nov. 1975.

Schulte W, "Centrifuged autologous blood for filling large bone defects: a modification to the autologous blood method", *Zentrifugiertes Eigenblut (Centrifuged Autologous Blood) DZZ 24*, vol. 10, pp. 854–857, 1969.

Schulte W, "Autologous Blood Filling: A new method in the treatment of major bone defects following oral surgery", *Eigenblutfullung Grosserer Knochendefekte DZZ 15*, vol. 12, pp. 910–914, 1960.

Rosenthal AR, Egbert PR, "Use of Platelet–Fibrinogen–Thrombin mixuture to seal experimental penetrating corneal wounds", *Graefes Archiv Ophthalmologie*, vol. 207, pp. 111–115, 1978.

Silverberg GD, Harbury CB, "A physiological sealant for cerebrospinal fluid leaks", *Journal of Neurosurgery*, vol. 46, pp. 215–219, Feb. 1977.

Pearl RM, Wustrack KO, "Microvascular Anastomosis using a blood product sealant–adhesive", *Surgery, Gynecology & Obstetrics*, vol. 144, pp. 227–231, Feb. 1977.

Arch Otorhinolaryngol, vol. 237, 1983, G. Wolf, "Der konzentrierte autologe Gewebekleber", p. 276–p. 283; p. 280; paragraphs 3–6; p. 281, paragraphs 1–3.

Wolf, Der Knozentrierte autologe Gewebekleber, Spring 1983, Arch Otorhinolaryngol, 237: pp. 279–283.

\* cited by examiner

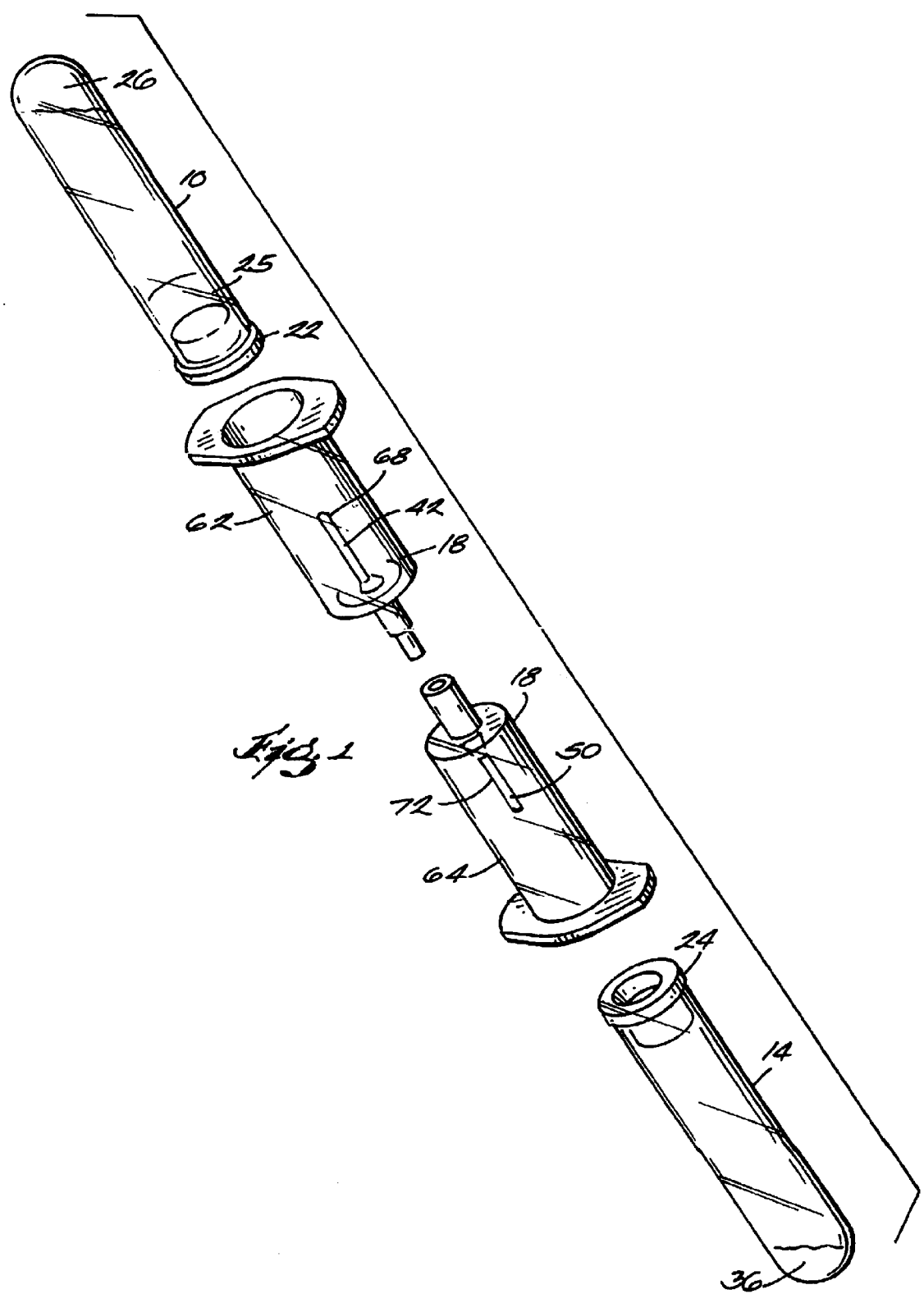

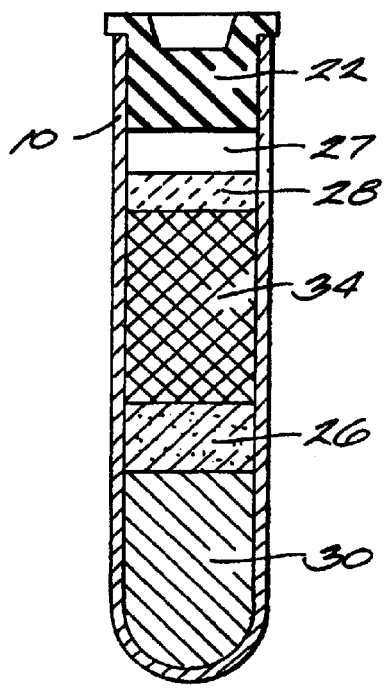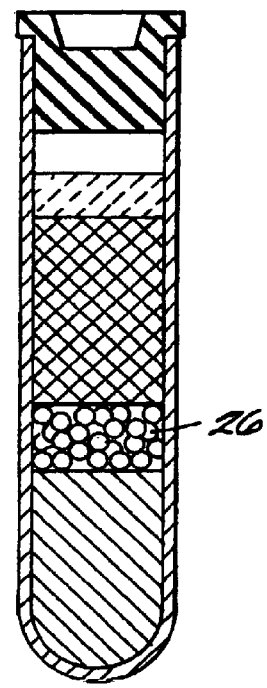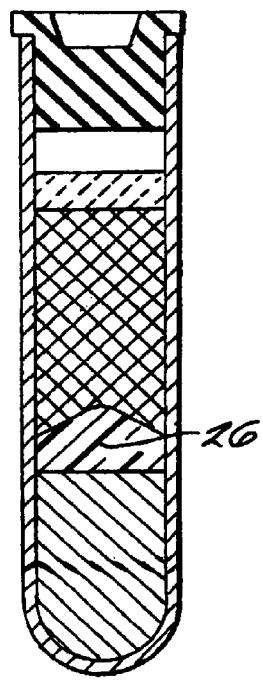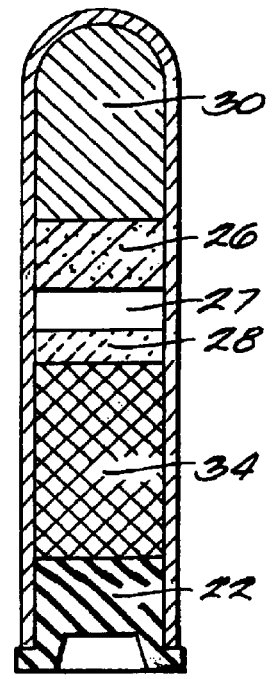

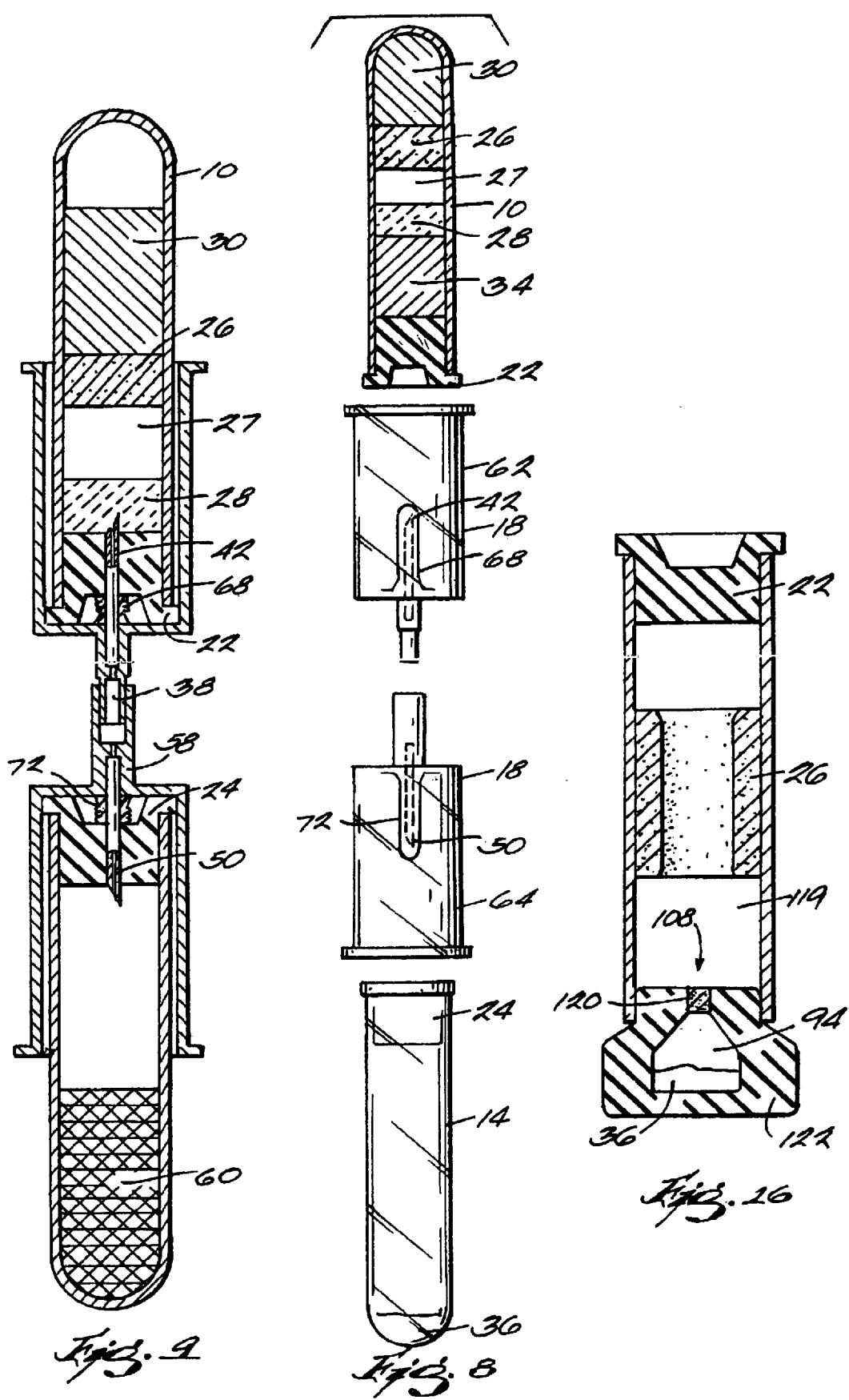

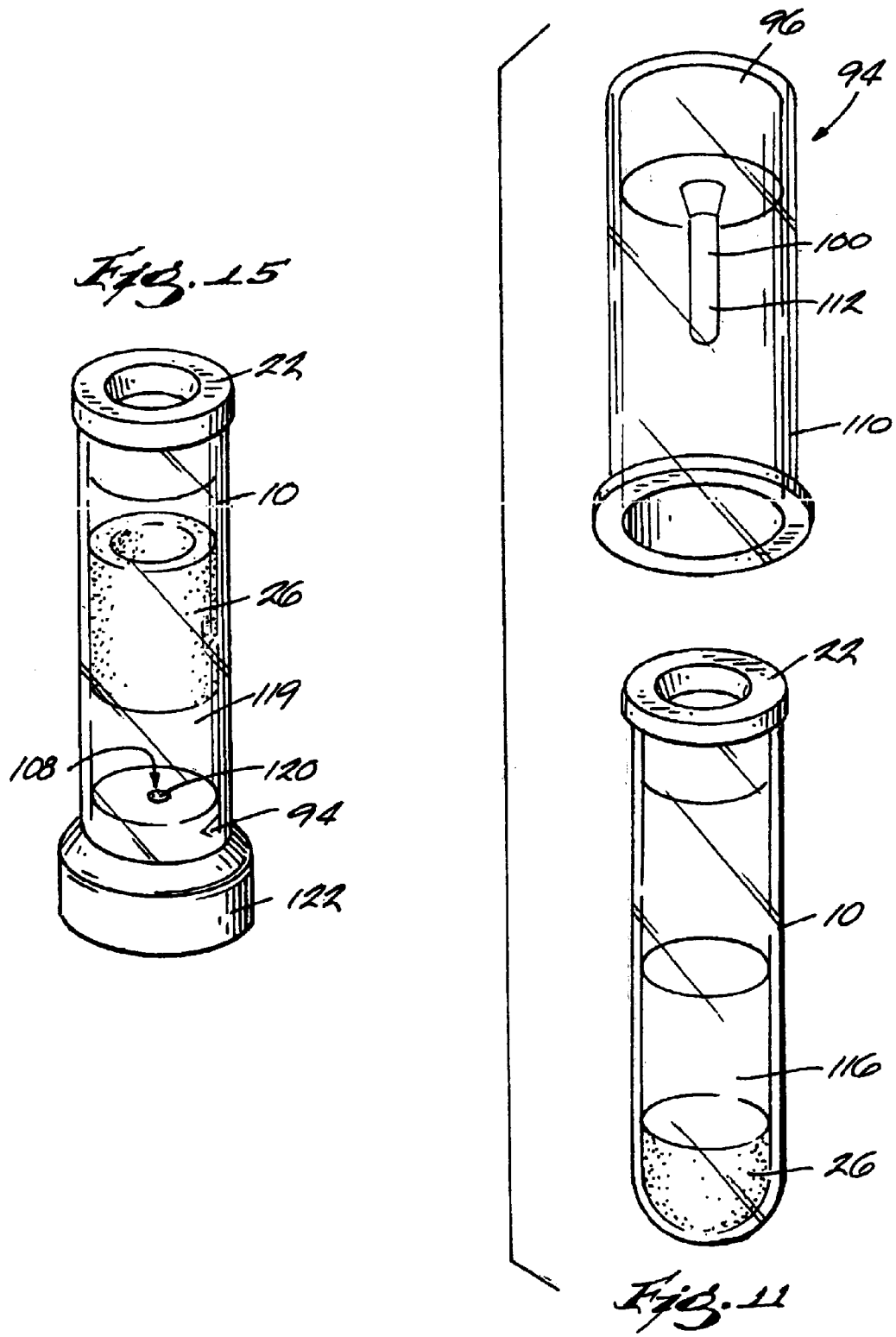

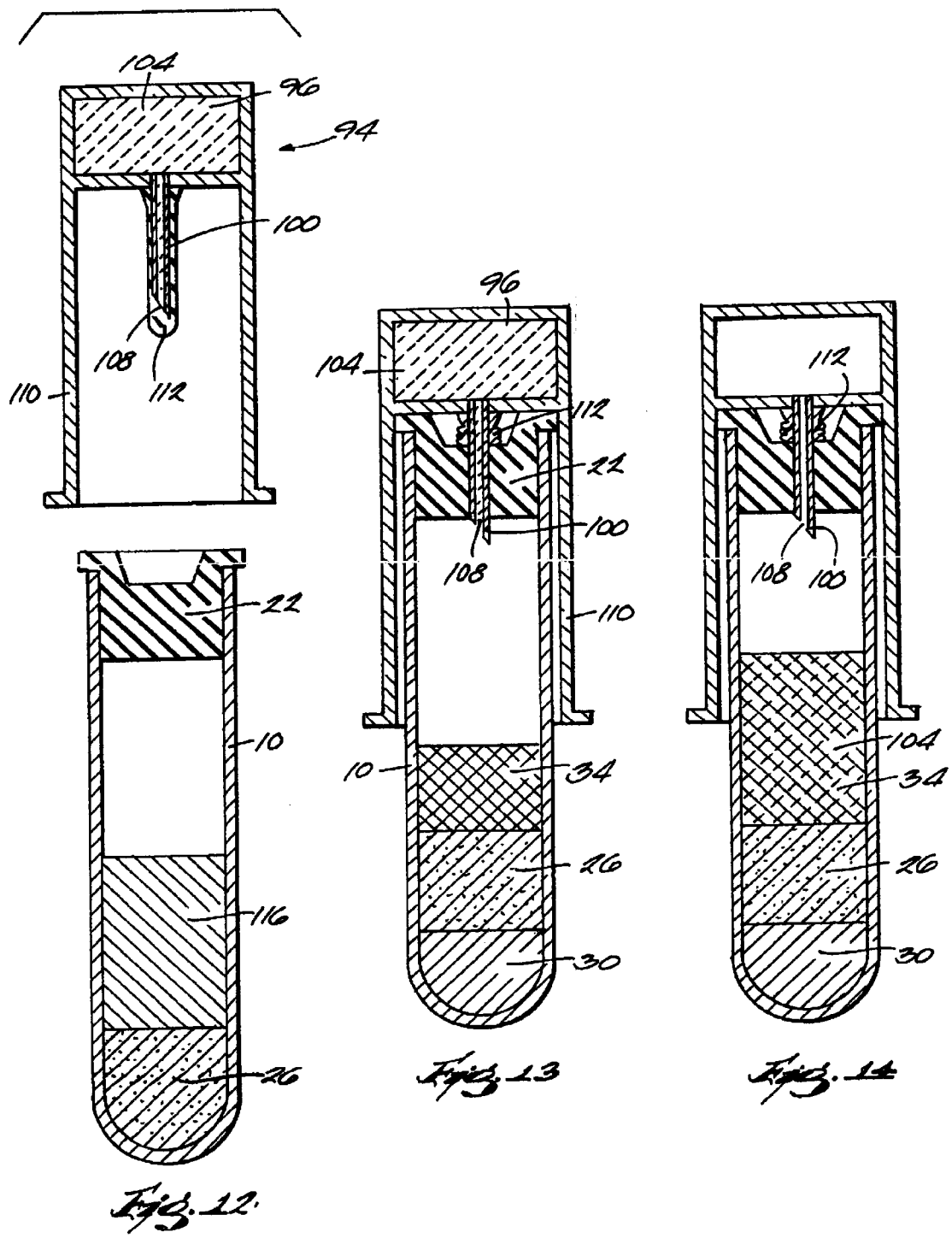

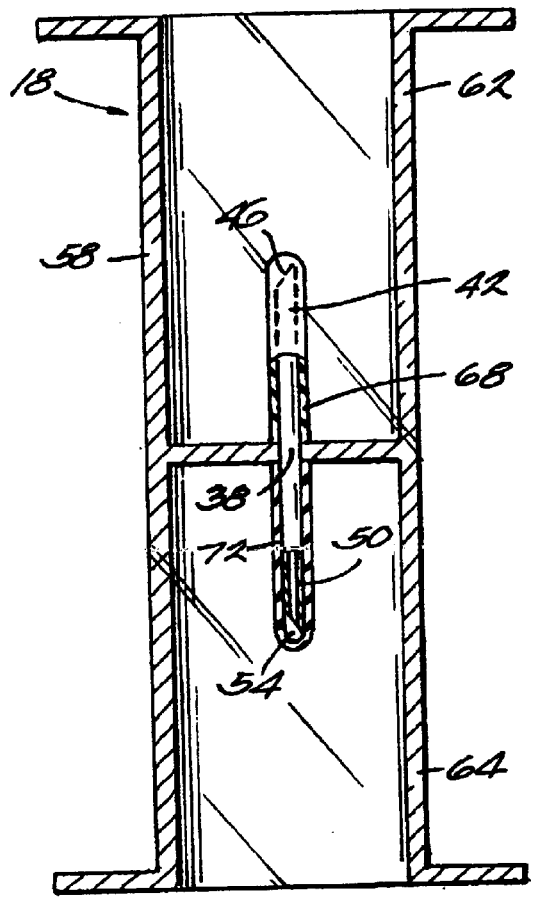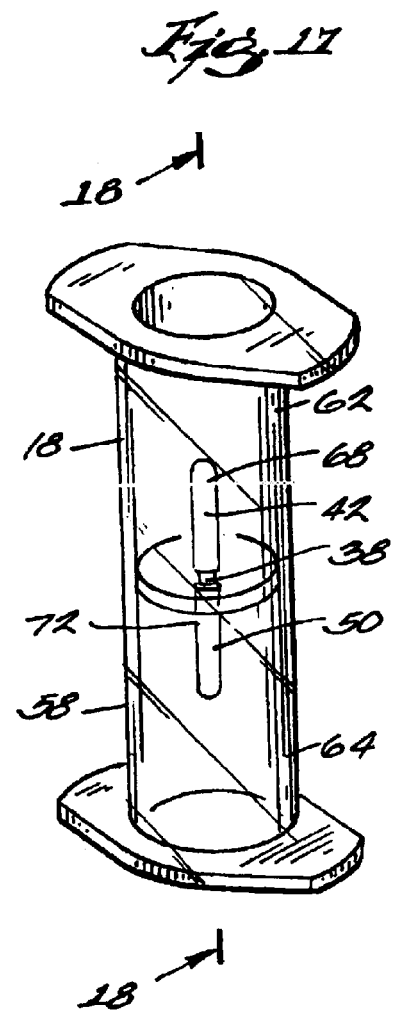

SYSTEMS AND METHODS FOR PREPARING AUTOLOGOUS FIBRIN GLUE

CROSS-REFERENCE TO RELATED APPLICATIONS

This application is a continuation-in-part of and claims priority to U.S. application No. 09/446,729 filed on Mar. 3, 2000 now U.S. Pat. No. 6,368,298, which is a 35 U.S.C. § 371 application of and claims priority to international application no. PCT/1T98/00173 filed Jun. 24, 1998, which claims priority to Italian application no. M197A001490 filed Jun. 24, 1997. This application claims priority to each of the applications mentioned above.

BACKGROUND OF THE INVENTION

The present invention relates to systems, kits and methods for preparing a solid-fibrin web or autologous fibrin glue.

Fibrin glue is known to be a haemoderivative largely that is used as a topical surgical adhesive or an haemostatic agent. Several kits are available on the market that contain concentrated fibrinogen from donors, associated to a proteic activator of human or animal origin, such as thrombin or batroxobin, for obtaining heterologous fibrin glue.

Such known kits involve the use of material of human or animal origin, which, owing to its origin, could result in possible viral contamination and in serious risks for the receiver of the fibrin glue. In the past the authorities have been compelled to suspend from trade or even ban the haemoderivatives obtained by using material of human or animal origin. Furthermore, rejection cases are known from the literature resulting from reimplanting fibrin produced by using human or animal proteins in patients. Such cases are indeed due to the heterologous origin, with respect to the receiver organism, of the sealant protein being reimplanted or some of the components used for preparing it.

The autologous fibrin glue, i.e. fibrin glue autologously obtained from a patient's own blood, is more reliable with respect to the rejection and/or infection risks. Several procedures have already been described for obtaining extemporary autologous fibrin glue, but no "ready to use" kit is available on the market although some relevant references can be found in the patent literature.

U.S. Pat. No. 5,733,545 discloses a plasma-buffy coat concentrate to be combined with a fibrinogen activator to form a platelet glue wound sealant. The method disclosed in this patent allows for a patient's blood to be processed in order to obtain autologous fibrin glue, but the methods use thrombin or batroxobin as the fibrinogen activator. These activators are of human or animal nature and therefore still involve the risk of rejection and/or viral infections for the patient.

U.S. Pat. No. 5,555,007 discloses a method and an apparatus for making concentrated plasma to be used as a tissue sealant. The method consists in separating plasma from whole blood and removing water from said plasma by contacting it with a concentrator to provide concentrated plasma which can be thereafter coagulated with a solution containing thrombin and calcium. The apparatus comprises a first centrifuge separator in a first chamber, a concentrator (e.g. dextranomer or polyacrylamide) included in a second chamber communicating with the first chamber, and a second separator. The method disclosed in this reference requires a long time for obtaining the plasma concentrate necessary for the subsequent preparation of autologous fibrin glue and the apparatus is expensive and not disposable. The method does not disclose using a calcium-coagulation activator, and requires a pre-concentration step.

Many methods and systems require the transfer of a fluid from one container to another. For example, many chemical and medical devices require the transfer of a requisite volume of liquid to be reacted sequentially with various reagents and specific volumetric aliquots. A common practice is to remove closures on two containers and to pipette liquid in one container to the other. This practice, however, exposes the sample to environmental contaminants. For example, this technique is used to transfer plasma that has been separated from red blood cells in a blood sample. A special technique is required, however, to remove the plasma at the interface meniscus. Frequently the high-density, undesirable, lower-fraction red blood cells contaminate the aspirated sample. To avoid this problem, the pipette is frequently maintained a safe distance from the meniscus (i.e. the separator between the plasma and red blood cells), thereby resulting in an incomplete transfer of the sample. The incomplete transfer of the desirable fraction results in lower than optimum volume yield and non-stoichiometric ratios of the sample reagents and those in the second container. This second condition can be a serious source of performance variation of the product. This is the case in many enzyme reactions in which reaction rates are a maximum at certain stoichiometric ratios and rapidly diminish at higher or lower ratios.

Overall, methods and systems for preparing autologous fibrin glue or a solid-fibrin which is capable of regenerating tissue in a living organism are desired.

BRIEF DESCRIPTION OF THE SEVERAL VIEW OF THE DRAWINGS

FIG. 1 is a perspective view of a first embodiment of the invention.

FIG. 2 is a cross-sectional view of a primary container of the first embodiment shown in FIG. 1.

FIG. 3 is a cross-sectional view of a different embodiment of the primary container of FIG. 2.

FIG. 4 is a cross-sectional view of a different embodiment of the primary container of FIG. 2.

FIG. 7 is a view similar to FIG. 2 showing the primary tube and its contents inverted.

FIG. 8 is a top plan view of the first embodiment shown in FIG. 1.

FIG. 9 is a partial cross-sectional view of FIG. 8 showing the primary container, secondary container and transfer device engaged, and the contents of the first container being transferred to the second container.

FIG. 11 is a perspective view of a second embodiment of the invention.

FIG. 12 is a cross-sectional view of the second embodiment of the invention shown in FIG. 11.

Figure 5:
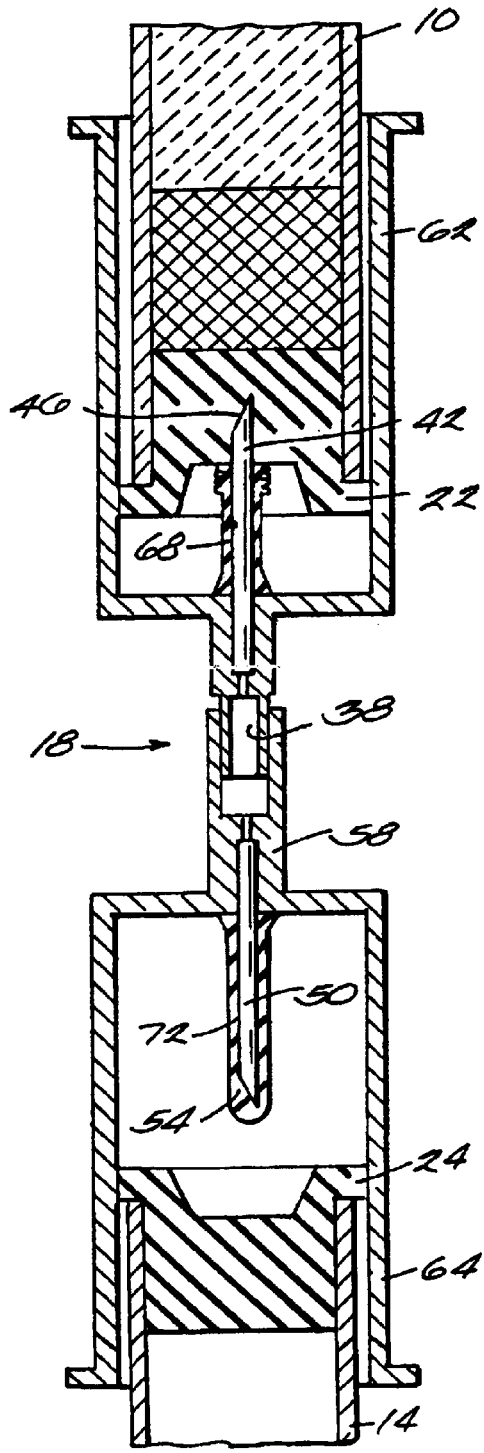
FIG. 5 is an enlarged partial cross-sectional view of a portion of the first embodiment in FIG. 1 depicting a first end of a transfer device beginning to puncture a sealed primary container.

FIG. 13 a cross-sectional view similar to FIG. 12 showing the reservoir and the primary collection device piercing the primary collection device.

FIG. 14 a cross-sectional view similar to FIG. 12 showing the reservoir piercing the primary collection device, and emptying its contents into the device.

FIG. 15 is a perspective view of a third embodiment of the invention.

FIG. 16 is a cross-sectional view of a third embodiment of the invention shown in FIG. 15.

FIG. 17 is a perspective view of a transfer device embodying the invention.

FIG. 18 is a cross-sectional view taken along line 18—18 in FIG. 17.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

SUMMARY OF THE INVENTION

In one aspect, the invention provides a system for preparing an autologous solid-fibrin web suitable for regenerating tissue in a living organism. The system comprises a sealed primary container containing a separation medium and a low-density high-viscosity liquid. The separation medium is capable of separating red blood cells from plasma when the container contains blood and is centrifuged, and the primary container has a first pressure. The system further comprises a sealed secondary container containing a calcium-coagulation activator. The secondary container has a second pressure that is less than the first pressure. The system also comprises a transfer device including a cannula having a first end and a second end. The first and second ends are capable of puncturing the sealed primary and secondary containers in order to provide fluid communication between the first and second containers. The low-density high-viscosity liquid of the primary container is capable of blocking flow through the cannula upon entering therein.

In another aspect, the invention provides another system for preparing a solid-fibrin web capable of regenerating tissue in a living organism. The system comprises a sealed primary container having a first pressure that is capable of having blood drawn therein. The system further comprises a sealed secondary container having a second pressure and containing a calcium-coagulation activator. The second pressure is less than the first pressure. The system also comprises a transfer device including a cannula having a first end and a second end. The first and second ends are capable of puncturing the sealed containers, and the transfer device is capable of transferring a portion of blood drawn in the primary container to the second container by pressure differentiation. The system also includes a centrifuge for concurrently centrifuging and coagulating the portion of blood transferred from the primary container to the secondary container through the transfer device and brought into contact with the calcium-coagulation activator in order to form a solid-fibrin web that is capable of regenerating tissue in a living organism.

In another aspect, the invention provides a method of preparing a solid-fibrin web for regenerating body tissue in a living organism. The method comprises drawing blood from a patient into a primary container and separating plasma from the blood in the primary container. Plasma from the primary container is transferred to a secondary container containing a calcium-coagulation activator using a transfer device comprising a cannula having a first end and a second end in order to contact the plasma with the calcium-coagulation activator. The plasma and calcium-coagulation activator are concurrently coagulated and centrifuged in the secondary container in order to form a solid-fibrin web. The solid-fibrin web is suitable for regenerating body tissue in a living organism.

In another aspect, the invention provides another system for preparing a solid-fibrin web suitable for regenerating tissue in a living organism. The system comprises a sealed primary collection device having an interior and containing a separation medium. The primary collection device is capable of having blood drawn into the interior, and the separation medium is capable of separating plasma from red blood cells when the primary collection device contains blood and is centrifuged. The system further comprises a reservoir having a chamber and a conduit in fluid communication therewith. The chamber has a calcium-coagulation activator therein, and the conduit is at least partially filled with a blocking medium to prevent the activator from flowing out of the chamber under ambient conditions.

In another aspect, the invention provides another method of preparing a solid-fibrin web capable of regenerating tissue in a living organism. The method comprises drawing blood from a patient into a primary collection device having a seal and providing a reservoir including a chamber and a conduit in fluid communication with the chamber. The chamber is at least partially filled a calcium-coagulation activator, and the conduit is at least partially filled with a blocking medium to prevent the activator from flowing out of the chamber under ambient conditions. The reservoir is connected to the primary collection device such that the chamber, conduit and collection device would be in fluid communication but for the blocking medium. The primary collection device is then centrifuged at a first rate. The first rate is sufficient to separate plasma from blood, yet not sufficient to move the blocking medium in the conduit into the primary collection device. The primary collection device is then centrifuged at a second rate. The second rate is sufficient to move at least a portion of the blocking medium from the conduit into the primary collection device, thereby allowing the calcium-coagulation activator to flow into the collection device and contact the plasma, thereby forming a solid-fibrin web suitable for regenerating tissue in a living organism.

DETAILED DESCRIPTION OF THE INVENTION

This application is a continuation-in-part of and claims priority to U.S. application Ser. No. 09/446,729 filed on Jul. 13, 2001 which issued as U.S. Pat. No. 6,368,298, which is a 35 U.S.C. § 371 application of and claims priority to international application no. PCT/IT98/00173 filed Jun. 24, 1998, which claims priority to Italian application no. MI97A001490 filed Jun. 24, 1997, each of which is hereby fully incorporated by reference.

The object of the present invention is therefore to provide a ready-to-use kit, allowing autologous fibrin glue to be rapidly obtained and not resulting in viral infections and/or rejection cases when used in surgery.

Such an object is achieved by using a coagulation activator, being neither of human nor of animal origin, but rather an inorganic compound which therefore cannot be infected and does not result in rejection.

The "ready to use" kit according to the present invention comprises a sealed container containing calcium chloride as coagulation activator. Calcium chloride activates the fibrinogen present in patient's plasma when this is introduced into the sealed container.

The systems and kits according to the present invention have the great advantage of allowing the preparation of autologous fibrin glue which may be used with no risk of viral infections or rejection cases. Another advantage of the kit according to the present invention is that it allows the preparation of autologous fibrin glue from patient's plasma in a very short time as well as in the formation of clots or membrane or spray. Still another advantage of the ready-to-use kit according to the present invention is that it allows the autologous fibrin glue to be obtained at costs proportionally lower with respect to the known systems.

Further advantages of the kit according to the present invention will be evident to those skilled in the art from the following detailed description of some embodiments thereof.

Containers suitable for the kit according to the present invention include a glass container for antibiotics as hereinafter described in Example 1. Also glass or plastic test-tubes may be used. The preferred volume of the container is from 5 to 15 ml. The test-tubes have preferably a diameter ranging from 12 to 16 mm and a height ranging from 75 to 100 mm. The container should be suitably thick in order to withstand the stresses resulting from the pressure difference between its inner space and the atmosphere when it is evacuated. Hemispherical or conical bottom tubes are preferably 0.7 mm thick, flat bottom tubes 1 mm thick. The plastic containers are preferably made of transparent polyester resin, 0.2–0.8 mm thick, in order to ensure the vacuum keeping for at least 12 months after production. After the preparation, the plastic test-tubes, are preferably introduced into a tin-foil vacuum air-tight container having a heat-sealed inner polyethylene layer in order to ensure a perfect air-tightness until the date of use.

It should be noted that the evacuation of containers or test-tubes is advisable, however not necessary for putting the present invention into practice.

The containers or test-tubes are sealed by rubber or silicon pierceable caps, being suitable to ensure the container to be perfectly air-tight and to allow the vacuum plugging after the introduction of the chemical components and before the steam or radiation sterilization step.

After the sealing, the containers may be sterilized under steam at 121° C. for 30 minutes. The sterilization may be carried out also by irradiation with gamma rays or electron beam.

While a fibrin stabilizer tranexamic acid can be used, pure and crystalline epsilon-amino-caproic acid is also suitable. The amount will be about 1 g when using a 25 ml container, suitable for a plasma amount of 20 ml. Sometimes it is not necessary to use a fibrin stabilizer.

As a coagulation activator, solid $CaCl_2.2H_2O$ or a liquid solution containing calcium is used in the kit according to the present invention although other coagulation activators (listed below) can be used. For example, 11.76 mg of $CaCl_2.2H_2O$ will be introduced in a 5 ml container, by using a precision dosimeter (maximum error: 1–2 mg), in order to prevent polluting foreign components to be introduced.

In case of a 15 ml container for a plasma amount of 12 ml, the solid dehydrated calcium chloride amount to be introduced will be as high as 35.28 mg, while the tranexamic acid amount will proportionally be as high as 300 mg of crystals.

In case of a 25 ml container for a plasma amount of 20 ml, the dehydrated calcium chloride amount to be introduced will be as high as 58.8 mg while the tranexamic acid amount will proportionally be as high as 500 mg of crystals.

Besides the dehydrated form used in the Examples, the calcium chloride may be in any other suitable form available on the market, e.g. as $CaCl_2.2H_2O$. Also a solution of this salt can be used, as described in Example 1.

EXAMPLES

Example 1

In a 5 ml glass container for antibiotics, being sealable under vacuum, made of transparent white glass, inert and 1 mm thick were introduced 100 mg of tranexamic acid, acting as fibrin stabilizer. The synthetic tranexamic acid, being more than 98% pure, is put on the market by the American company Sigma Inc. Separately, a 1M $CaCl_2$ solution was prepared, by weighing on a precision balance 147.0 g of $CaCl_2.2H_2O$ (>99%pure), from the same American company Sigma Inc.

This salt was dissolved in exactly 1 liter of ultrapure nonpyrogenic distilled water, for a few minutes at room temperature, under frequent stirring. By using a precision piston dispenser, having a dispensing precision of ±5% (Eppendorf like), 80 µL of the activator solution were introduced in the glass container. In this step, at the same time as the dispensing, a filtering was carried out by using a 0.22µm Millpore sterilizing filter, while carefully preventing possible contamination from powders or filaments of any kind. Finally the glass container was plugged with a rubber cap being pierceable and pluggable under vacuum, while minding not to completely plug the container, so as to allow the subsequent vacuum plugging and possibly a further sterilization by using gas. The container was then introduced into a suitable device for vacuum plugging, while preventing any possible contamination from solid particles in the atmosphere (ULPA or HEPA filtration in sterile chamber). A vacuum as high as 4 ml was applied, by using a membrane vacuum pump and a micrometric control, to the inner atmosphere of the device. In order to control the vacuum level in the inner atmosphere, a precision vacuum gauge was used (precision #1 mbar). Finally, without discharging the device, the container was plugged under vacuum, to be thereafter recovered for the use as described in the following Example.

Example 2

10 ml of venous blood were drawn from a patient according to the provisions of the qualitative standards for clinical analysis, e.g. by using VACUTAINER® sterile test-tubes by Becton-Dickinson, added with a 0.106 M sodium citrate solution. For this purpose also test-tubes added with disodium or dipotassium ethylenediaminetetraacetate can be used.

The sample was carefully kept sterile during the blood drawing. Finally, the sample was gently shaken for wholly mixing the components, thereby ensuring the anticoagulating action of sodium citrate. The test-tube was then introduced in a suitable centrifuge, while carefully balancing the rotor weight in order to prevent the same centrifuge to be damaged. Once the lid is sealed, the sample was centrifuged at 3500 rpm for 15 minutes, thereby separating the red cells (being thicker) from the citrated plasma (supernatant). In this case the plasma yield, mainly depending upon the characteristics of the donor blood, was as high as 55%. The test-tube containing the separated plasma was kept plugged in sterile conditions and was placed vertically in a stand for recovering the plasma itself, in this step care was taken not to shake the test-tube, in order to prevent the mixing of the two phases separated in the centrifugation. The outer portion of the test-tube cap was then sterilized by using denatured alcohol and then a sterile needle, being connected to a sterile syringe, was introduced in the test-tube cap. The needle was brought up to 3–4 mm apart from the separating meniscus of the two phases, and 4 ml of plasma were drawn. By using the same needle, the cap of the container according to the present invention, which had been prepared as described in Example 1, was pierced, having been previously sterilized by using alcohol. As soon as the needle pierced the cap, the citrated plasma contained in the syringe was completely sucked into the container. This was gently shaken and, after about 2 minutes at 37° C., a clot of sterile autologous fibrin glue was obtained, ready to be immediately used.

Example 3

About 18 ml of venous blood were drawn from a normotype 49 years-old patient by using 5 ml sodium citrate VACUTAINER® test-tubes by Becton-Dickinson, taking care to shake gently just after the drawing of the sample. The so taken blood was immediately subjected to centrifugation (15 min. at 2500 rpm) to separate the plasma. The plasma (12 ml) was carefully transferred into two 10 ml test-tubes, containing 120 μL of $CaCl_2$ (10 g/100 ml) each, which had been prepared as described in Example 1, but without using tranexamic acid. After mixing the plasma with the activator, the test-tubes were centrifuged for 30 min. at 3000 rpm, finally obtaining two massive fibrin samples which were inserted, with all sterility precautions, within 2–3 hours from preparation, in the large vesicular mandibular cavity resulting from extraction of impacted left canine and right second incisor, as well as from abscission of the cyst present in the central area of the incisor teeth. Finally the gingival edges were closed with eight stitches. A radiographic check 15 days after showed the fibrin still in its position, apparently intact. Histology 7 months after proved the complete replacement of the fibrin with bony tissue, with a better post-operative course than with traditional methods, requiring over 12 months to achieve the same result. Since no antifibrinolytic agent had been used for the preparation of autologous fibrin, it can be stated in this case that said additive was useful for the specific purpose.

Example 4

To produce an adhesive fibrin glue 12 ml of plasma, obtained as in Example 3, were transferred, with all the measures in order to preserve sterility, into a 20 ml container according to the present invention, prepared as described in Example 1.

After careful stirring, the mixed plasma was poured on a sterile glass slide, of the kind used in chemical laboratories, where the plasma was mixed with sterile and very pure calcium carbonate of coralline origin (BIOCORAL™•NOTEBS S.A. France), or with calcium fluoride (>98% Sigma Inc.). These calcium salts are both well known to the skilled in the art as stimulators of fibroblasts.

By mixing one part of the plasma with one part of calcium carbonate, (e.g.; 2 ml with 500 mg) a malleable, sterile and adhesive paste was obtained and used as a filler for subgingival spaces or different cavities after abscission of' infected mucous sacs. The paste, positioned so as to fill the empty spaces, formed in a few minutes a solid fibrin web acting as a haemostatic plug and created an autologous biological substrate supporting the mucous edges in position and where later migration of connectival cells started.

Example 5

To obtain a membrane of fibrin glue 20 ml of plasma, obtained as in Example 3, were put in a 25 ml, flat-bottomed container according to the present invention prepared as in Example 1. After the usual careful stirring, the container was centrifuged for 40 min. at 4000 rpm with a swing-out rotor. At the end of the centrifuging operation, from the bottom of the test tube a white-colored, very compact and tensile-strong membrane was recovered, having the same size as the bottom of the test-tube (24 mm diam.) and thickness of 3 mm. This autologous membrane, owing to its compactness and strength, was used as a holding and separating membrane in dental and general surgery, as a substitute for porous synthetic membranes. The obtained membrane can be stored sterile for several days at 4° C.

Example 6

To obtain large-sized membranes of fibrin glue about 200 ml of citrated plasma were drawn from a patient, collected and separated in a double transfusion bag. The plasma was subjected to cryoprecipitation by freezing at −80° C. for 12 hours, defreezing being carried overnight at 4° C. (this procedure k well known to those skilled in the art). The same morning the plasma obtained by this procedure was subjected to centrifugation for 15 min. at 5000 rpm at 4° C. to obtain about 20 ml of cryoprecipitate. After careful removal of the supernatant by using a pressing device (e.g. XP100 of the company Jouan S.A. France) the cryoprecipitate was taken up with 20 ml of whole plasma of the same patient. The resulting 40 ml were put in a 35 mm diameter, flat-bottomed sterile polypropylene container according to the present invention, containing the suitable quantity of activator, as in Example 1. After careful shaking, the container was centrifuged for 40 min. at 5000 rpm to obtain a membrane as in Example 5, but more compact and tensile-strong owing to the higher content of fibrin. Said membrane too can be stored in sterile form for several days at 4° C.

The membrane obtained by the method described in Example 5, in addition to utilization described in Example 4, can be used as a substrate for the culture in vitro of dermal cells of the same patient, in order to obtain grafts to be transplanted in case of very serious scalds.

Membranes of a good quality useful for the above mentioned purposes can be obtained also from whole separated plasma directly transferred into the container according to the present invention. The obtained membrane will be thinner than the above described one, but still useful for surgical uses and as a substrate for cellular growth.

Example 7

To obtain spray fibrin starting from a cryoprecipitate as in Example 5, 20 ml of cryoprecipitate were taken up with 10 ml of whole plasma at room temperature and gently shaken, to complete dissolution. The resulting plasma was carefully transferred into a 50 ml container according to the present invention prepared as in Example 1, shaking gently for a perfect mixing of the components. After 120 sec. at room temperature, the test-tube was connected to a Venturi-type sterile air compressor, known to those skilled in the art, to be uniformly distributed on the surface of a bleeding organ being subjected to surgery (lung, heart, spleen, arterious anastomosis). The concentrated plasma, containing concentrated fibrinogen, thrombin, calcium ions and other coagulation enzymes, distributed over the organ, coagulated within a few seconds, owing also to tissue coagulation activating enzymes present in the endothelium of the patient creating a fibrin film having a protective haemostatic function. The surgical operation was therefore concluded with the reduction of internal hemorrhages and so avoiding further blood transfusions or complications.

The present invention also provides systems and methods for forming a solid-fibrin web or autologous glue capable of regenerating tissue in a living organism. In these methods and systems, anticoagulated plasma is obtained by centrifugation of a blood sample. The transfer devices described herein enable the plasma to be transferred to a second container containing calcium-clotting agents and then immediately centrifuged in order to obtain a stable, dense, autologous fibrin and platelet network. The transfer devices described herein may also be used to transfer other liquids in other applications. In other words, the transfer devices and systems described herein enable concurrent centrifugation and coagulation. By using these systems and methods several advantages may be achieved: 1) the sample is manipulated in a manner by which sterility is maintained; 2) the total volume of plasma is transferred to maximize a full yield of a clot; 3) the stoichiometric ratio of anticoagulant and calcium clotting agent is maintained in a narrow range to minimize clotting time; 4) the transfer is completed quickly; 5) health care providers not normally performing these operations (e.g. dentists) can easily perform these methods and operate the systems; and 6) the devices are single use in order to prevent reuse and possible contamination by blood-borne pathogens.

Generally speaking, the invention provides integrated systems and methods for preparing a solid-fibrin web or autologous glue which can be used to regenerate tissue in a living organism. In one embodiment (shown in FIG. 1), the system comprises a primary container 10, a secondary container 14 and a transfer device 18. Preferably, the primary and secondary containers 10, 14 are tubes, and more particularly, test tubes, although any container that is capable of holding a fluid or liquid and being centrifuged is suitable for use with the invention. Preferably, the containers 10, 14 are made from glass or plastics.

The primary container 10 must be capable of drawing blood therein using standard venipuncture techniques. Preferably the primary container 10 is sealed with a seal 22 while the blood is being drawn to prevent contamination, although the container 10 may be sealed shortly thereafter. A variety of seals 22 can be used to seal the primary container 10, e.g., a rubber stopper, cap, foam, elastomer or other composite. The seal 22 should be capable of being pierced or punctured, and therefore rubber and silicone are preferred materials from which the seal is fabricated, although any material that provides a seal and is capable of being pierced can be used. The primary container 10 may contain an anticoagulant solution 25. The anticoagulant 25 in the solution preferably comprises a calcium-binding agent. More particularly, the anticoagulant 25 may comprise sodium citrate, ethylenelendiaminetetraacetic acid disodium salt, ethylenelendiaminetetraacetic acid dipotassium salt and tripotassium and combinations thereof. Preferably, the primary container 10 contains a sodium citrate solution. The anticoagulant 25 tends to thin blood collected in the primary container 10 in order to place it in condition for centrifugation. In addition, the primary container includes a density-gradient separation medium 26, air 27 as well as a high-viscosity, low-density fluid 28 (see FIG. 10 which shows a kit further described below).

The density-gradient separation medium 26 must be capable of separating different fractions of a particular liquid or fluid in the primary container 10 having different densities. The separation medium 26 allows for dense, unwanted fractions of the liquid to be separated by centrifugation, and subsequently removed. For example, the separation medium 26 may separate red blood cells 30 from platelet-rich plasma 34 during centrifugation of a blood sample. In one example, the separation medium 26 may be found in the bottom of the primary container 10. In other examples, the separation medium 26 may be applied as a ring around the interior of the primary container 10, or any other suitable interior position. Although any density-gradient separation medium 26 capable of separating liquids having different densities during centrifugation is suitable for use with the invention, preferably the medium 26 is a gel, and more preferably, a thixotropic gel. FIG. 2 illustrates the primary container 10 after centrifugation of a blood sample has taken place, and also shows the gel separation medium 26. Preferably, the thixotropic gel has a sufficient yield point such that it does not flow in or move about the primary container 10 at ordinary ambient conditions, but does flow at higher centrifugal forces experienced during centrifugation. Most preferably, a gel having a density that is less than the high density of the unwanted red blood cell fraction 30, but greater than the density of the desired plasma fraction 34 is preferred. In other words, most preferred is a gel or other medium that is capable of separating red blood cells 30 from plasma 34 after a blood sample is centrifuged. Such a medium 26 will move or flow within the container during centrifugation, but does not flow thereafter, thereby creating a semi-permanent barrier between separated fractions when centrifugation is complete.

As shown in FIG. 3, another suitable density-gradient separation medium 26 which can be employed in the primary container 10 is a plurality of plastic beads 26 possessing the desired density for fraction separation. The beads may be suspended in the high viscosity, low-density fluid required for later sealing the transfer device 38. During centrifugation, the beads 26 migrate to the interface between the two fractions 30, 34 and are compacted, much like sintering, to form a stable barrier between the fractions having different densities (i.e. red blood cells 30 and the plasma 34). The residual high-viscosity, low-density fluid that coats the pellets contributes to the stability of the compacted layer.

Other suitable density-gradient separation medium include polymeric float devices such as those disclosed in U.S. Pat. Nos. 5,560,830 and 5,736,033 issued to Coleman, which are hereby incorporated by reference. FIG. 4 shows a polymeric float device 26.

The low-density, high-viscosity immiscible fluid 28 ("LDHV fluid") in the primary container generally comprises an inert oil. Most preferably, the LDHV fluid is polyester, silicone or another inert fluid, and is applied to the primary container in a position above the gel by displacement or pressure pumps. The LDHV fluid must be capable of blocking or eliminating flow through the cannula 38 of the transfer device 18 upon entry therein as further described below.

The secondary container 14 (shown, inter alia, in FIGS. 1 and 10) contains the chemical reagents necessary for particular reactions. The second container 14 is sealed by a seal 24 in a similar manner as the first container 10, i.e. by a rubber stopper, cap, foam, elastomer or other composite. In one application of the invention as discussed below, the secondary tube may contain a calcium-coagulation activator 36. Examples of suitable calcium-coagulation activators include, but are not limited to, calcium chloride, calcium fluoride, calcium carbonate and combinations thereof, however, any salt containing calcium will suffice as a calcium-coagulation activator. In addition, other activators include calcium gluconate, calcium fumarate, calcium pyruvate and other organic calcium salts that are soluble in water and are compatible with human life. The coagulation activator coagulates the plasma when it comes in contact therewith. The secondary container 14 may be fully evacuated to an internal pressure that is substantially zero. Evacuating the secondary container 14 facilitates the transfer of fluid from the primary container 10 to the secondary container 14 through the transfer device 18. Because no gas molecules are present as the secondary container 14 is filled during transfer, there is no compression of the residual gas with resulting pressure increase. As a result, the flow rate is maximized, complete transfer is facilitated, sterility is maintained by eliminating the need for venting and the desired stoichiometric ratio for the desired reaction is maintained.

In another embodiment, the secondary container may also contain one or more of an antibiotic, an analgesic, a cancer therapeutic, a platelet-growth factor and a bone morphogenic protein. Other therapeutic agents which can be topically administered may also be included. Examples of antibiotics include, but are not limited to, ampicillin, erythromycin and tobramycin. Analgesics include, but are not limited to, aspirin and codeine. Cancer therapeutics include, but are not limited to, 5-fluor-uracile.

Figure 6:
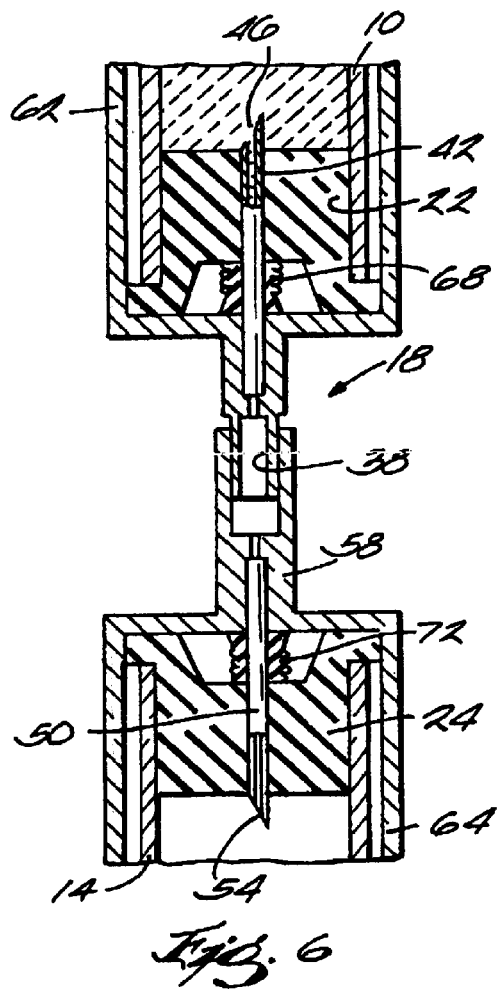
FIG. 6 is a view similar to that set forth in FIG. 5 depicting the first end of the transfer device fully puncturing the sealed primary container and a second end of the transfer device fully puncturing a sealed secondary primary container.

The transfer device 18 may comprise two pieces as shown, e.g., in FIG. 1 or, alternatively, may be one piece as shown, e.g., in FIGS. 17–18. A one-piece, single-molded transfer device 18 is preferred. As best shown in FIGS. 5–6 and 17–18, the transfer device 18 comprises a cannula 38 having a first end 42 having a first opening 46 and a second end 50 having a second opening 54. The ends 42, 50 of the cannula 38 are sharp or pointed (or even have a bevel ground on them) so as to be able to puncture or penetrate the seals 22, 24 of the primary and secondary containers 10, 14. The cannula 38 is recessed and coaxially mounted within the housing 58 in order to prevent accidental finger stick during manipulation of the containers. The housing 58 has two cylindrical, opposed guides 62, 64 which are centrally and axially oriented with the cannula 38. The guides 62, 64 serve to guide the primary and secondary containers 10, 14 onto the first and second ends 42, 50 of the transfer device 18. FIGS. 5 and 6 show the guides 62, 64 guiding the containers 10, 14 onto the first and second ends 42, 50.

The ends 42, 50 of the cannula 38 may be encompassed or covered by safety valves, sheaths or elastomeric sleeves 68, 72, which form a hermetic seal. The safety sheaths 68, 72 also cover the first and second openings 46, 54. When the first and second ends 42, 50 puncture the elastomeric sleeves 68, 72, the sleeves 68, 72 retract accordingly. FIG. 5 shows the first end 42 beginning to puncture the seal 22 of the primary container 10 and the sleeve 68 being retracted accordingly, while sleeve 72 still fully covers the second end 50. The ends 42, 50 extend far enough to fully puncture the seals 22, 24, but not extend much further into the containers 10, 14 (as shown in FIG. 6). This allows maximum volume transfer of the inverted primary container's 10 liquid volume to the secondary container 14. FIG. 6 also shows the first and second ends 42, 50 having fully punctured the seals 22, 24 of the first and second containers 10, 14, and both of the sleeves 68, 72 being fully retracted. The elastomeric sleeves 68, 72 prevent the flow of gas or liquid when not punctured. Suitable materials for the sleeves 68, 72 include, but are not limited to, rubber varieties and thermoplastic elastomers.

Turning now to the operation of the first embodiment, once blood has been drawn into the primary container 10 using standard venipuncture techniques, the blood is anti-coagulated by the anti-coagulant 25 therein. Typically, the primary container 10 is sealed while the blood is being drawn, however, it may be sealed thereafter. Sealing the primary container 10 prevents contamination of the contents therein. Thereafter, the primary container and its contents 10 (i.e. blood, anti-coagulant 25, separation medium 26 and LDHV fluid 28) are centrifuged. Acceptable centrifugation can take place at a gravitational force in the range of 900 to 3,500× G for 5 to 15 minutes. In a preferred embodiment, the primary container is centrifuged at a gravitational force of about 1,000× G for about ten minutes. This initial centrifugation separates the primary container's contents or fractions into a plurality of layers as shown, e.g., in FIG. 2. The layers include (in order from the bottom of the primary container 10 to the top of the container after centrifugation): the red blood cell layer 30, the separation medium 26, the platelet-rich plasma layer 34, the LDHV fluid layer 28, and finally a residual gas 27 volume at a pressure equal to atmospheric. The proportions of these layers may vary from application to application, and are shown here in these proportions for illustrative purposes only. Subsequent to centrifugation, the sealed primary holder 10 is inverted before the transfer device 18 is used to puncture the seal 22. In other words, the primary container 10 is inverted such that the sealed opening is in the lowest vertical position as shown in FIG. 7. Inverting the primary container changes the order in which the layers are arranged. Above the seal 22 are the following layers in sequence from bottom to top: the platelet-rich plasma 34, the high-viscosity, low-density immiscible fluid 28, the residual gas 27, the separation medium 26 and the red blood cells 30.

Next, the secondary container 14 is placed in a vertical position with its sealed opening 24 in the topmost position as best shown in FIG. 8. This positions the secondary container 14 for the transfer of the primary holder's contents therein. FIG. 8 illustrates the centrifuged primary container 10 in the inverted position above the transfer device 18, which is above the secondary container 14 in the proper position for transfer. The transfer device's guide 64 is then placed over and guides the secondary container 14 therein, while the inverted primary container 10 is then placed into the other guide 62 (or vice-versa). In other words, either end 42, 50 of the cannula 38 can be used to puncture either seal 22, 24. Because the transfer device 18 is symmetrical on either end, the user is provided a degree of foolproof operation. The user then forces the containers together in order puncture both seals 22, 24 with each respective cannula end 42, 50. The two valve sleeves 68, 72 covering the ends 42, 50 further enhance the foolproof operation. First, if the first end 42 punctures the primary seal 22 (again, either end can be used to puncture either seal), the unpunctured sleeve 72 covering the other end 50 will contain the fluid, thereby preventing the fluid from spilling. On the other hand, if the other end 50 punctures the other seal 24 (and the sleeve 72 accordingly) first, the vacuum is maintained by the sleeve 68 covering the first end 42.

Once the ends 42, 50 puncture both sleeves 68, 72 and seals 22, 24 as shown in FIGS. 6 and 9, the desired fluid is transferred from the primary container 10 to the secondary container 14 by pressure differential. In other words, because the pressure in the secondary container 14 has been evacuated, the contents (more particularly, the plasma 34) of the primary container 10 flow into the secondary container 14. The pressure in the primary container 10, originally at atmospheric, decreases as the liquid level diminishes and the gas volume expands. At no point, however, is the pressure equal to zero. Because the secondary container 14 is fully evacuated to a pressure equal to zero, the pressure therein does not increase as the tube is filled since there is no gas to compress. Accordingly, the apparatus 18 may be used to transfer a wide variety of liquids and solutions from one tube to another, and should not be construed to be limited only to the transfer of blood.

Because of the particular sequential arrangement of the layers in the primary container 10, the platelet-rich plasma 34 is easily transferred. In addition, because the primary container 10 is also preset to an evacuation level, the container only partially fills after blood collection. This allows the gas in the "head space" to remain significantly above zero during transfer when its volume is expanded, thereby allowing fast and complete transfer to the secondary container 14. This is dictated by the ideal gas law and the Poiseuille-Hagen equation.

Transfer of the contents or fragments of the primary container (i.e. the platelet-rich plasma) continues until the LDHV fluid 28 enters the cannula 38. The LDHV fluid's high viscosity plugs the narrow lumen of the cannula 38, thereby resulting in flow discontinuance. This prevents reuse of the transfer device 18, which is particularly important in trying to eliminate contaminated blood transfer devices, and also prevents accidental contamination by blood borne pathogens by prior use on or by another patient.

The transfer of the plasma fraction 34 to the secondary container 14 is complete, thereby allowing maximum yield and maintenance of the appropriate stoichiometric ratio of reagents. The plasma 34 then contacts the coagulation activator 36 in the second container 14, thereby creating a mixture 60 which can be immediately centrifuged to form a solid-fibrin web. The pressure differential between primary and secondary containers 10, 14 is substantially maintained throughout transfer, allowing rapid transfer. The transfer device 18 is unaffected by order of tube engagement, rendering the system virtually foolproof. Finally, the transfer occurs without venting, maintaining sterility and non-contamination of the sample.

Overall, the transfer device 18 provides a quick and efficient way of contacting the plasma 34 with the calcium-coagulation activator 36, immediately subsequent to which concurrent coagulation and centrifugation of the plasma can take place in order to form the solid-fibrin web. The solid-fibrin web is suitable for regenerating body tissue in a living organism. Such a method alleviates the need to first pre-concentrate the plasma by removing water therefrom before the plasma is contacted with the calcium-coagulation activator 36. In addition, the transfer device 18 can be used to transfer blood or other fluids in a wide variety of application.

Figure 10:
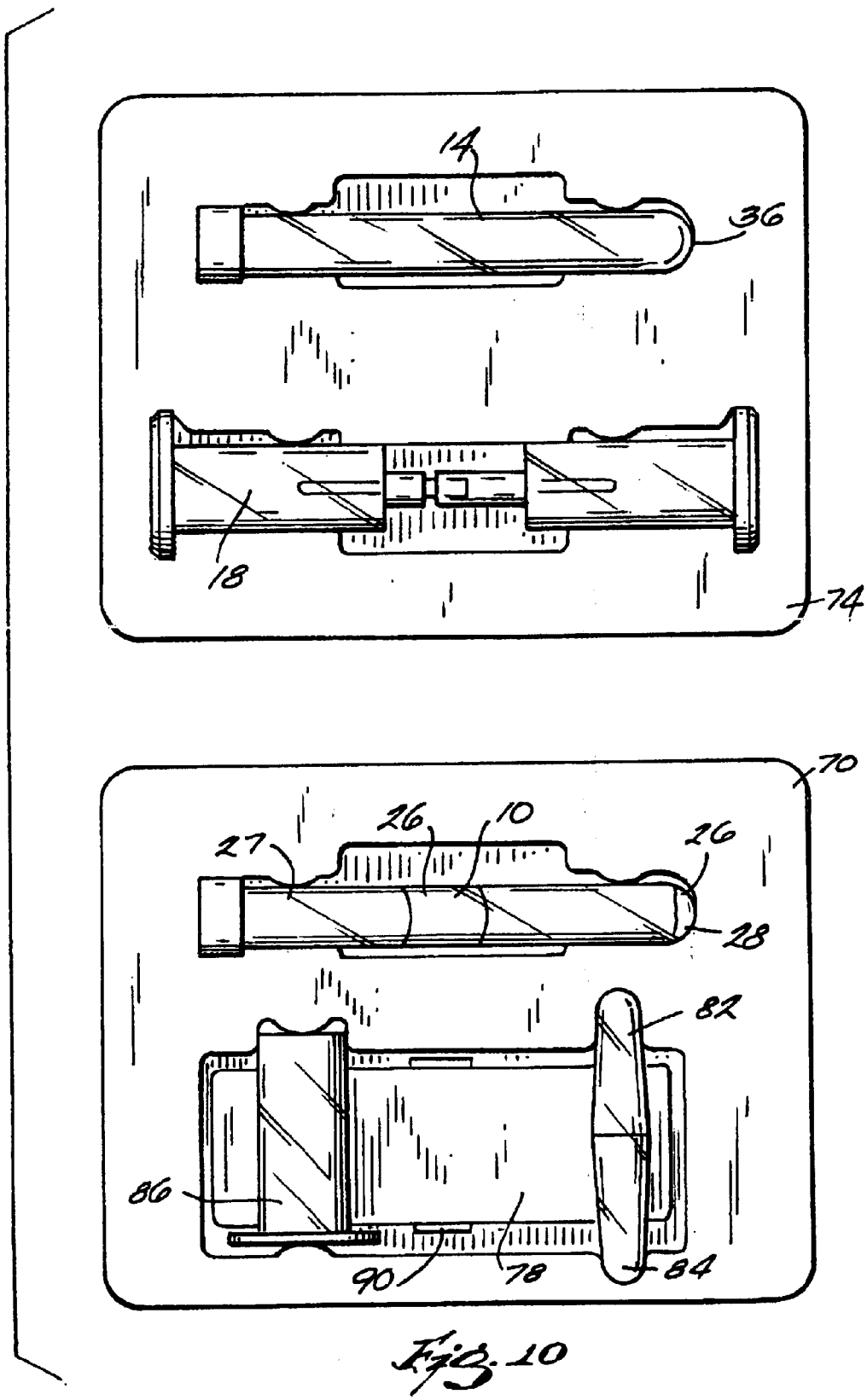
FIG. 10 is a top plan view of a kit embodying the invention.

The invention also provides a ready-to-use kit as shown in FIG. 10. The kit comprises the primary container 10, the secondary container 14 and the transfer device 18. In one embodiment of the kit, the kit may have two trays 70, 74 that lift out of a package. The first tray 70 has all the components necessary for Step 1 and the second tray 74 has all the components required for Step 2. Of course, the components can be arranged in a wide variety of manners.

Step 1 comprises collecting blood into the primary container 10, followed by centrifugation to obtain platelet-rich plasma. The components of the first tray 70 comprise an alcohol swab 78 to cleanse the venipuncture site, a multiple sample blood collection needle 82 (21 gauge×1 "), a safety holder 86, the primary container 10 containing the anticoagulant (e.g. citrate), gel, LDHV fluid and a bandage 90 to cover the venipuncture site. The venipunture site is cleansed with the sterile alcohol swab 78. The needle cartridge 84 is opened and screwed into the safety holder 86. The needle 82 is then inserted into the patient's vein and the container 10 is connected to the holder 86. Blood then fills the container, and the needle 82 is withdrawn and retracted into the holder 86. The end of the holder is closed with the hinged flap. The vein is closed with the bandage 90. The container 10 is centrifuged at about 1000×G for about 10 minutes and the plasma is separated from the red blood cells.

The components of the second tray are the components used for step 2 include an AFTube (Autologous Fibrin Tube) or secondary container 14 and a transfer device 18. Step 2 comprises placing the primary container 10 in an inverted position and into the transfer device 18. The secondary container 14 contains the coagulator and is punctured by the other end of the transfer device. The containers 10, 14 are joined and the platelet-rich plasma flows from the primary container 10 to the secondary container 14. The secondary container is then immediately centrifuged at 2300×G for about 30 minutes to obtain dense fibrin with platelets or a solid-fibrin web.

In a second embodiment of the invention, another integrated system for preparing a solid-fibrin web is provided as shown in FIGS. 11–14. The system comprises a primary collection device 10, which is very similar to the primary container 10 of the first embodiment. The collection device 10 may contain a density-gradient-cell separating medium 26 (as described above) and an anticoagulant (not shown) as well as a reservoir 94 that can be connected to the primary collection device 10 or integral therewith. The discussion above pertaining to the first embodiment of the invention, and more particularly, to the separation medium 26 applies to the second embodiment of the invention. In other words, the same materials can be used for the separation medium 26, and the same materials are preferred. For example, most preferably the separation medium 26 comprises a thixotropic gel, the yield point of which prevents it from flowing at ordinary ambient conditions, but allows it to flow at the higher centrifugal forces experienced during centrifugation. The separation medium 26 may be located at the bottom as shown in FIG. 11 (i.e. the opposite end from the opening) of the primary collection device. Alternatively, the separation medium may form a ring around the interior of the primary collection device. The primary collection device 10 is essentially the same as the primary container 10 described above, except that the primary collection device may not contain a high-density, low-viscosity fluid. Preferably, the primary collection device 10 has a seal 22 such as a rubber stopper or cap (as discussed above).

The reservoir 94 comprises a chamber 96 and a cannula 100 in fluid communication therewith. The chamber 96 contains a liquid reagent 104, most preferably a calcium-coagulation activator. Preferably, the calcium-coagulation activator is calcium chloride, calcium fluoride, calcium carbonate, calcium gluconate, calcium fumarate, calcium pyruvate or a combination thereof The cannula 96 must be capable of puncturing the seal 22 of the primary collection device 10. In a preferred embodiment, the cannula contains a blocking medium 108 such as a yield-point gel that prevents the reagents 104 in the chamber 96 from flowing out of the cannula 100 under ambient conditions. Other suitable blocking mediums include, but are not limited to, force-actuated mechanical systems such as balls on springs, valves, spring-loaded valves, pierceable membranes and ampoules (i.e. hollow membranes filled with fluids or powders). The yield point of the gel 108 is such that upon centrifugation at a particularly high gravitational force, the gel 108 moves in order to allow communication between the chamber 96 and the primary collection device 10 when the two are engaged. The reservoir 94 may also have a guide housing 110 used to guide the reservoir onto the collection device 10. The cannula 100 may be encompassed or covered by an elastomeric sleeve 112 to maintain sterility of the cannula 100. The sleeve 112 is discussed above with regard to the first embodiment.

In another embodiment, the chamber 96 may also contain one or more of an antibiotic, an analgesic, a cancer therapeutic, a platelet-growth factor and a bone morphogenic protein. Other therapeutic agents which can be topically administered may also be included. Examples of antibiotics include, but are not limited to, ampicillin, erythromycin and tobramycin. Analgesics include, but are not limited to, aspirin and codeine. Cancer therapeutics include, but are not limited to, 5-fluor-uracile.

In operation, a patient's blood 116 is collected into the primary collection device 10 by conventional venipuncture technique as described above. The anticoagulant in the primary collection device 10 thins the blood before centrifugation. Subsequently, the reservoir 94 is then attached to the primary collection device 10 by piercing the cannula 100 of the reservoir 94 through the seal 22 of the primary collection device 10 as shown in FIGS. 13 and 14. The sleeve 112 retracts when the cannula 100 pierces the seal 22. The length of the cannula 100 is sufficient to puncture the seal 22, but the cannula preferably does not extend much further into the collection device 10, although it could.

The collection device 10 and the reservoir 94 are then centrifuged. The centrifugal force exerted on the tube is described by the equation $F=\omega m r^2$; where F=force, m=mass of system, r=radial distance from the center of the rotor, and $\omega$=is the rate of angular rotation. Since the reservoir is at a smaller r than the primary tube gel, the gel in the reservoir's cannula cannot move since insufficient shear stresses are generated. The primary tube 10 spins at the low gravitational force until the cells separate and the gel 26 moves to the cell/plasma interface as shown in FIG. 13. In other words, similar to the first embodiment, the separation medium 26 separates the red blood cells 30 from the platelet-rich plasma 34 after an initial centrifugation at about 1000×G for about 10 minutes. Centrifugation at a centrifugal force of about 900–1500×G for about 5 to 15 minutes is also acceptable for the initial centrifugation.

Subsequently, the centrifuge speed is increased and the reservoir experiences sufficiently high gravitational force such that the blocking medium 108 in the cannula 100 empties into the primary collection device 10 and the liquid reagent 108 (e.g. the calcium-coagulation activator) is emptied from the reservoir as shown in FIG. 14. The contents may subsequently be centrifuged at about 2300–6000×G for about 15–40 minutes. As the calcium-coagulation activator contacts the plasma in the primary collection device, immediate and concurrent coagulation and centrifugation occurs because the sample is still being centrifuged. This results in the formation of a solid-fibrin web suitable for the regeneration of tissue. The operation of primary tube cell separation and subsequent addition of the liquid clotting agent at the right stoichiometric ratio is performed in one tube without transfer. By programming the centrifuge with regard to speed and duration, the invention provides a simple and foolproof process.

In an alternative embodiment, the single collection device 10 has an interior compartment 119 and a reservoir 94 as shown in FIGS. 15–16. The reservoir 94 is integral with or connected to the primary collection device 10 and in fluid communication with the compartment. A tube, conduit or opening 120 provides the fluid communication between the compartment 119 and the reservoir 94, and is sealed with the blocking medium 108. Again, the blocking medium 108 has a yield point that is activated and moves when exposed to a particularly high gravitational force in order to allow communication between the reservoir 94 and the primary collection device 10 as described above. The gel or medium's yield point is such that it does not move during initial centrifugation to separate blood cells from the plasma. In the third embodiment, each end of the device has an opening and each end is sealed by a removable or non-removable seal 22, 122 such as a rubber stopper, cap, foam, elastomer or other composite. The reservoir 94 with stopper 122 is located at the opposite end of the collection device's seal 22 and opening.

In another embodiment, the reservoir 94 may also contain one or more of an antibiotic, an analgesic, a cancer therapeutic, a platelet-growth factor and a bone morphogenic protein. Other therapeutic agents which can be topically administered may also be included. Examples of antibiotics include, but are not limited to, ampicillin, erythromycin and tobramycin. Analgesics include, but are not limited to, aspirin and codeine. Cancer therapeutics include, but are not limited to, 5-fluor-uracile.

The alternative embodiment is used in the same manner as described above with respect to the second embodiment, i.e., the centrifuge is controlled at two different centrifugal forces: 1) the first being a force sufficient to separate the plasma from the red blood cells; and 2) the second being a force sufficient to move the blocking medium 108 in the tube, conduit or opening 120 between the reservoir and the interior of the device and into the main body. As a result, the calcium-coagulation activator is allowed to enter the interior of the device. This in turn enables concurrent centrifugation and coagulation of the plasma in order to form the solid-fibrin web as centrifugation proceeds at the second, higher gravitated force. The seal 122 may be removed in order to obtain the solid-fibrin web or autologous glue. In a preferred embodiment, the seal 122 is threaded and can be screwed out of the device 10 as shown in FIG. 16.

We claim:

1. A system for preparing an autologous solid-fibrin web suitable for regenerating tissue in a living organism, the system comprising:

a sealed primary container containing a separation medium capable of separating red blood cells from plasma when the container contains blood and is centrifuged, the primary container having a first pressure;

a sealed secondary container containing an ionic coagulation activator, the secondary container having a second pressure that is less than the first pressure; and a transfer device capable of providing fluid communication between the first and second containers, wherein the separation medium is at least one of a gel, beads and a float device.

2. The system of claim 1, wherein the secondary container is evacuated.

3. The system of claim 1, wherein the ionic coagulation activator is selected from calcium chloride, calcium fluoride, calcium carbonate, calcium gluconate, calcium fumarate, calcium pyruvate and combinations thereof.

4. The system of claim 1, wherein the primary container further contains an anti-coagulant.

5. The system of claim 1, wherein the secondary container contains one or more of an antibiotic, an anelgesic, a cancer therapeutic, a platelet-growth factor and a bone morphogenic protein.

6. A system for preparing an autologous solid-fibrin web suitable for regenerating tissue in a living organism, the system comprising:
 a sealed primary container containing a separation medium capable of separating red blood cells from plasma when the container contains blood and is centrifuged, the primary container having a first pressure;
 a sealed secondary container containing an ionic coagulation activator, the secondary container having a second pressure that is less than the first pressure; and
 a transfer device capable of providing fluid communication between the first and second containers,
 wherein the transfer device comprises a cannula having a first end and a second end, the first and second ends being capable of puncturing the sealed primary and secondary containers, and
 wherein the first and second ends are each covered by an elastomeric sleeve, the elastomeric sleeve being retractable when the first or second ends puncture the primary or secondary sealed containers.

7. The system of claim 6, wherein the secondary container is evacuated.

8. The system of claim 6, wherein the ionic coagulation activator is selected from calcium chloride, calcium fluoride, calcium carbonate, calcium gluconate, calcium fumarate, calcium pyruvate and combinations thereof.

9. The system of claim 6, wherein the primary container further contains an anti-coagulant.

10. The system of claim 6, wherein the secondary container contains one or more of an antibiotic, an analgesic, a cancer therapeutic, a platelet-growth factor and a bone morphogenic protein.

11. A system for preparing an autologous solid-fibrin web capable of regenerating tissue in a living organism, the system comprising:
 a sealed primary container having a first pressure, the primary container being capable of having blood drawn therein;
 a sealed secondary container having a second pressure and containing an ionic-coagulation activator, the second pressure being less than the first pressure; and
 a transfer device capable of puncturing the sealed containers, the transfer device being capable of transferring a portion of blood drawn in the primary container to the second container by pressure differentiation,
 wherein the primary container contains a separation medium, a high-viscosity-low-density fluid and an anticoagulant, and wherein the separation medium is at least one of gel, beads and a float.

12. The system of claim 11, wherein the ionic coagulation activator is selected from calcium chloride, calcium fluoride, calcium carbonate, calcium gluconate, calcium fumarate, calcium pyruvate and combinations thereof.

13. The system of claim 11, wherein the secondary container contains one or more of an antibiotic, an analgesic, a cancer therapeutic, a platelet-growth factor and a bone morphogenic protein.

14. The system of claim 11, wherein the transfer device comprises a cannula having a first end and a second end, and wherein the first and second ends are each covered by an elastomeric sleeve, the elastomeric sleeve being retractable when the first and second ends puncture or secondary sealed containers.

15. The system of claim 11, wherein the secondary container is evacuated.

* * * * *

UNITED STATES PATENT AND TRADEMARK OFFICE
CERTIFICATE OF CORRECTION

PATENT NO. : 6,979,307 B2
DATED : December 27, 2005
INVENTOR(S) : Roberto Beretta and Nicholas A. Grippi It is certified that error appears in the above-identified patent and that said Letters Patent is hereby corrected as shown below:

Column 17,
Line 2, delete "anelgesic" and insert -- analgesic --.

Column 18,
Line 33, after "puncture" insert -- the primary --.

Signed and Sealed this

Twenty-eighth Day of March, 2006

JON W. DUDAS
*Director of the United States Patent and Trademark Office*